United States Patent
Nogami et al.

(10) Patent No.: US 12,246,032 B2
(45) Date of Patent: Mar. 11, 2025

(54) STABILIZED AQUEOUS COMPOSITION COMPRISING CHONDROITIN SULFATE AND HYALURONIC ACID

(71) Applicant: Seikagaku Corporation, Tokyo (JP)

(72) Inventors: Eiji Nogami, Tokyo (JP); Akira Koushinbou, Tokyo (JP); Noriko Oshima, Tokyo (JP); Kota Fujiwara, Tokyo (JP); Tomoya Sato, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

(21) Appl. No.: 17/834,796

(22) Filed: Jun. 7, 2022

(65) Prior Publication Data

US 2022/0296634 A1    Sep. 22, 2022

Related U.S. Application Data

(63) Continuation of application No. 16/935,922, filed on Jul. 22, 2020, now abandoned, which is a continuation of application No. 16/073,301, filed as application No. PCT/JP2017/002858 on Jan. 27, 2017, now abandoned.

(30) Foreign Application Priority Data

Jan. 29, 2016    (JP) .................. 2016-015630

(51) Int. Cl.
*A61K 31/737* (2006.01)
*A61K 9/00* (2006.01)
*A61K 31/728* (2006.01)
*A61K 47/26* (2006.01)
*A61K 47/36* (2006.01)

(52) U.S. Cl.
CPC .......... *A61K 31/737* (2013.01); *A61K 9/0048* (2013.01); *A61K 31/728* (2013.01); *A61K 47/26* (2013.01); *A61K 47/36* (2013.01)

(58) Field of Classification Search
None
See application file for complete search history.

(56) References Cited

U.S. PATENT DOCUMENTS

| | | |
|---|---|---|
| 6,051,560 A | 4/2000 | Chang et al. |
| 2005/0215516 A1* | 9/2005 | Bucolo .............. A61L 31/10 623/4.1 |
| 2015/0352143 A1 | 12/2015 | Gavard |

FOREIGN PATENT DOCUMENTS

| | | |
|---|---|---|
| EP | 0 136 782 | 3/1992 |
| EP | 2 596 796 A1 | 5/2013 |
| EP | 2 540 284 | 6/2017 |
| JP | H01-21133 | 4/1985 |
| JP | H08-291057 | 11/1996 |
| JP | H09-227385 | 9/1997 |
| JP | H10-072376 | 3/1998 |
| JP | H11-302197 | 11/1999 |
| JP | 2005-060234 A | 3/2005 |
| JP | 2007-530226 | 11/2007 |
| JP | 2012-031122 | 2/2012 |
| JP | 2012-031123 | 2/2012 |
| JP | 2012-046442 | 3/2012 |
| JP | 2013-014586 | 1/2013 |
| WO | WO-2005/097226 | 10/2005 |
| WO | WO-2014/110454 | 7/2014 |

OTHER PUBLICATIONS

Hoare, T. et al "Rheological blends for drug delivery . . . " J. Biomed. Mater. Res., vol. 92A, 575-585. (Year: 2010).*
Maltese, A. et al "Novel polysaccharides-based viscoelastic formulations . . . " Biomaterials, vol. 27, pp. 5134-5142. (Year: 2006).*
Alcon Japan Ltd, "VISCOAT® 0.5 Ophthalmic Viscoelastic Substance" Jan. 2014 revision (9th edition, revision due to change of storage temperature), 10 pages (Including English translation).
Beaman et al., "The scientific basis for the duration of stability data required at the time of submission," J Pharma Sci (2010) 99(6) 2538-2543.
International Search Report for PCT/JP2017/002858, dated Feb. 21, 2017, pages.
Legre-Boyer, "Viscosupplementation: techniques, indications, results," Orthop Traumatol Surg Res (2015) 101(1 Suppl):S101-108.
Mongkhon et al., "Sorbitol-modified hyaluronic acid reduces oxidative stress, apoptosis and mediators of inflammation and catabolismin human osteoarthritic chondrocytes," Inflamm Res (2014) 63(8):691-701.
Rivera et al., "Effectiveness of intra-articular injections of sodium hyaluronate-chondroitin sulfate in knee osteoarthritis: a multicenter prospective study," J Orthop Traumatol (2016) 17(1):27-33.

* cited by examiner

*Primary Examiner* — Leigh C Maier
(74) *Attorney, Agent, or Firm* — MORRISON & FOERSTER LLP

(57) ABSTRACT

The present invention relates to an aqueous composition which comprises chondroitin sulfate, hyaluronic acid, and a pharmaceutically acceptable carrier, and which can be stored at room temperature.

The present invention also relates to an aqueous composition which comprises chondroitin sulfate, hyaluronic acid, sorbitol, and a pharmaceutical acceptable carrier.

13 Claims, No Drawings

STABILIZED AQUEOUS COMPOSITION COMPRISING CHONDROITIN SULFATE AND HYALURONIC ACID

CROSS-REFERENCE TO RELATED APPLICATIONS

This application is a continuation of U.S. patent application Ser. No. 16/935,922 filed Jul. 22, 2020, which is a continuation of U.S. patent application Ser. No. 16/073,301 filed Jul. 26, 2018, which is a U.S. National Stage of International Application No. PCT/JP2017/002858 filed Jan. 27, 2017, which claims priority from Japanese Patent Application No. 2016-015630 filed Jan. 29, 2016, the contents of each of which are incorporated herein by reference in their entirety.

TECHNICAL FIELD

The present invention relates to an aqueous composition which comprises chondroitin sulfate, hyaluronic acid, and a pharmaceutically acceptable carrier and which can be stored at room temperature. More particularly, the present invention relates to an aqueous composition containing chondroitin sulfate, hyaluronic acid, and sorbitol.

BACKGROUND ART

Currently, a viscoelastic agent containing chondroitin sulfate sodium and sodium hyaluronate (VISCOAT®) is commercially available as an ophthalmic surgical aid.

This commercial viscoelastic agent is known to have poor stability at room temperature and decrease in viscosity during storage. It is also known that this viscoelastic agent is instable to light, and decreases in viscosity through exposure to light. Thus, since being approved by the United States in 1986, VISCOAT® has been required to be stored under the following conditions: "protect from light, protect from freezing, store in cold place (2 to 8° C.)" (Non-Patent Document 1).

Patent Document 1 relates to a method for stabilizing an aqueous ophthalmic solution containing hyaluronic acid. Patent Document 2 relates to a stabilized composition containing hyaluronic acid. However, these documents are silent on a method for stabilizing an aqueous composition per se containing chondroitin sulfate and hyaluronic acid.

Meanwhile, an aqueous composition containing chondroitin sulfate and hyaluronic acid is known to exhibit a high viscosity which cannot be predicted from the viscosity of each component alone (Patent Document 3). It has been proposed that the mechanism of exhibiting such an increased viscosity is based on interaction between chondroitin sulfate and hyaluronic acid. However, the details of the mechanism have not yet been elucidated. Therefore, the respective facts known for chondroitin sulfate and hyaluronic acid are not directly applicable when it comes to the properties, in particular the viscosity, of the above-mentioned composition.

Actually, even though about 30 years have passed since the approval of VISCOAT®, there has yet been no formulation in practical use which can be stored at room temperature or without protection from light. In addition, no method has ever been reported for stabilizing the viscosity of an aqueous composition containing chondroitin sulfate and hyaluronic acid. This attests to the particularity of this composition, that is, the respective facts known for chondroitin sulfate and hyaluronic acid are not directly applicable to this composition.

PRIOR ART DOCUMENTS

Patent Documents

Patent Document 1: Japanese Patent Application Laid-Open (kokai) No. 1998-72376
Patent Document 2: Japanese Patent Application Laid-Open (kokai) No. 1999-302197
Patent Document 3: U.S. Pat. No. 6,051,560

Non-Patent Documents

Non-Patent Document 1: package insert of VISCOAT®

SUMMARY OF THE INVENTION

Problems to be Solved by the Invention

VISCOAT®, a pre-filled syringe preparation of an aqueous composition containing chondroitin sulfate sodium and sodium hyaluronate, must be stored in a cold place as it decreases in viscosity by storage at room temperature (the interview form of VISCOAT®). Generally, handling of pre-filled syringe preparations which are required to be stored under cold conditions is cumbersome because it is necessary to control temperature during transport thereof, secure a storage site in a medical facility, and keep the preparations at room temperature for a certain period of time before use. However, there has never been reported a method for stabilizing the composition itself, possibly due to the particularity of its properties.

Thus, an object of the present invention is to provide a stabilized aqueous composition containing chondroitin sulfate and hyaluronic acid. Particularly, the object of the invention is to provide such an aqueous composition that is stable even at room temperature.

Another object of the present invention is to provide a method for stabilizing or storing such a composition, or a method for producing such a composition which is stabilized.

Means for Solving the Problems

The present inventors have found that a drop in viscosity of an aqueous composition containing chondroitin sulfate and hyaluronic acid can be suppressed even at room temperature by including sorbitol in the composition. The present invention has been accomplished on the basis of this finding. Accordingly, the present invention is directed to an aqueous composition which comprises chondroitin sulfate, hyaluronic acid, and a pharmaceutically acceptable carrier and which can be stored at room temperature. The present invention is also directed to an aqueous composition containing chondroitin sulfate, hyaluronic acid, and sorbitol.

<1> An aqueous composition which comprises chondroitin sulfate, hyaluronic acid, and a pharmaceutically acceptable carrier and which can be stored at room temperature.

<2> An aqueous composition which comprises chondroitin sulfate, hyaluronic acid, sorbitol, and a pharmaceutically acceptable carrier.

<3> The composition according to <1> or <2>, which comprises 20 to 60 mg/mL of chondroitin sulfate and 10 to 40 mg/mL of hyaluronic acid.

<4> The composition according to any one of <1> to <3>, which comprises chondroitin sulfate and hyaluronic acid as active ingredients, and sorbitol as an additive.

<5> The composition according to any one of <2> to <4>, wherein the sorbitol is D-sorbitol.

<6> The composition according to any one of <1> to <5>, which has a viscosity of 20,000 to 120,000 mPa·s at 25° C. and at a shear rate of 2 $s^{-1}$.

<7> The composition according to any one of <2> to <6>, which can be stored at room temperature.

<8> The composition according to any one of <1> to <7>, which is a viscoelastic agent.

<9> The composition according to any one of <1> to <8>, which is an ophthalmic composition.

<10> The composition according to any one of <1> to <9>, which is an ophthalmic surgical aid.

<11> The composition according to any one of <1> to <10>, which is an ophthalmic viscoelastic agent.

<12> The composition according to any one of <1> to <11>, which is clear and colorless.

<13> The composition according to any one of <1> to <12>, which is an injection.

<14> A method for stabilizing the composition as recited in any one of <1> to <13>, the method comprising including sorbitol in the composition.

<15> A method for producing the composition as recited in any one of <1> to <13>, the method comprising including sorbitol in the composition.

<16> A method for storing the composition as recited in any one of <1> to <13>, the method comprising including sorbitol in the composition.

<17> The storage method according to <16>, which comprises storing the aqueous composition at room temperature.

<18> A method for treating an ocular disease, which comprises administering, to a patient in need of an ophthalmic surgical aid in an ophthalmic surgery, an effective amount of the aqueous composition as recited in any one of <1> to <13>.

<19> The method according to <18>, which comprises: storing the aqueous composition as recited in any one of <1> to <13> at room temperature, and administering, to a patient in need of an ophthalmic surgical aid in an ophthalmic surgery, an effective amount of the aqueous composition stored at room temperature.

<20> Use of the aqueous composition as recited in any one of <1> to <13> in manufacture of an ophthalmic surgical aid employed in an ophthalmic surgery for treating an ocular disease.

<21> The use according to <20>, wherein the aqueous composition is an aqueous composition for use in an ophthalmic surgery after storage thereof at room temperature.

<22> The aqueous composition according to any one of <1> to <13>, which is for use as an ophthalmic surgical aid employed in an ophthalmic surgery for treating an ocular disease.

<23> The aqueous composition according to <22>, which is for use in an ophthalmic surgery after storage thereof at room temperature.

Effects of the Invention

Inclusion of sorbitol in an aqueous composition containing chondroitin sulfate and hyaluronic acid can suppress a drop in viscosity of the aqueous composition. It also allows the composition to be stably stored for a long period of time. As a result, the aqueous composition containing chondroitin sulfate and hyaluronic acid no longer needs to be stored at a cold site, and can be stored at room temperature. For example, the composition can be stored even at a temperature higher than 8° C. In addition, in one embodiment of the aqueous composition of the present invention, a drop in viscosity of the aqueous composition can be suppressed even under exposure to light.

MODES FOR CARRYING OUT THE INVENTION

Definitions

The terms used herein are defined as follows.

Unless otherwise specified, "chondroitin sulfate" (also abbreviated as "CS") refers to chondroitin sulfate or a salt thereof. The term "chondroitin sulfate sodium" is used with the same meaning as "sodium chondroitin sulfate ester."

Unless otherwise specified, "hyaluronic acid" (also abbreviated as "HA") refers to hyaluronic acid or a salt thereof.

Unless otherwise specified, the term "molecular weight" refers to weight average molecular weight.

Unless otherwise specified, the term "viscosity" refers to a viscosity as determined at 25° C. and a shear rate of 2 $s^{-1}$.

Any numerical range represented by "X to Y" herein refers to a range including X as the minimum value and Y as the maximum value. In the case where a composition contains a plurality of substances that correspond to each component, the content of each component in the composition refers to, unless otherwise specified, the total amount of those substances in the composition.

(1) Composition of the Present Invention

The composition of the present invention is an aqueous composition which comprises CS, HA, and a pharmaceutically acceptable carrier and which can be stored at room temperature. Furthermore, the composition of the present invention is an aqueous composition which comprises CS, HA, sorbitol, and a pharmaceutically acceptable carrier.

<CS>

CS is not particularly limited so long as it is a glycosaminoglycan which has a basic backbone in which disaccharide structural units consisting of D-glucuronic acid residues bonded with N-acetyl-D-galactosamine residues via β-1,3 bonding are repeatedly bonded via β-1,4 bonding, wherein some of the hydroxyl groups of the disaccharide structural units are sulfated. CS may be in a free form (i.e., a non-salt form) or may form a pharmaceutically acceptable salt. CS may be a non-cross-linked CS.

CS may be derived from natural products, chemically synthesized, or produced by culturing a microorganism or by genetic engineering techniques. For example, when CS is obtained from a natural product, the natural product to be source material may be appropriately chosen in accordance with the desired type of CS and other factors. Alternatively, CS of interest may be obtained by appropriately modifying a natural product-derived substance via chemical synthesis techniques.

The weight average molecular weight of CS is not particularly limited, but is, for example, 10,000 to 100,000, and preferably 10,000 to 60,000, more preferably 15,000 to 50,000, still more preferably 15,000 to 40,000, and particularly preferably 15,000 to 25,000. The weight average molecular weight of CS may be determined by the light scattering technique.

<HA>

HA is not particularly limited so long as it is a glycosaminoglycan which has a basic backbone in which disaccharide structural units consisting of D-glucuronate residues bonded with N-acetyl-D-glucosamine residues via β-1,3-bonding are repeatedly bonded via β-1,4 bonding. HA may be in a free form (i.e., a non-salt form) or may form a pharmaceutically acceptable salt. HA may be a non-cross-linked HA.

HA may be chemically synthesized, produced by culturing a microorganism or by genetic engineering techniques, or derived from a natural product extracted from a part of a living body, such as cockscomb, umbilical cord, cartilage, or skin.

The weight average molecular weight of HA is not particularly limited, but is, for example, 10,000 to 5,000,000, and preferably 200,000 to 3,000,000, more preferably 300,000 to 2,000,000, still more preferably 400,000 to 1,200,000, yet more preferably 400,000 to 900,000, particularly preferably 450,000 to 800,000, and yet more preferably 500,000 to 750,000. The weight average molecular weight of HA herein may be determined by measuring intrinsic viscosity in accordance with the "viscosity measurement method" of The Japanese Pharmacopeia 16th Revision and calculating with the equation of Laurent et al. (Biochim. Biophys. Acta, 42, 476(1960)).

<Pharmacologically Acceptable Salts of CS and HA>

Pharmacologically acceptable salts of CS or HA include, for example, alkali metal ion salts such as sodium salt and potassium salt, and alkaline earth metal ion salts such as magnesium salt and calcium salt. From the viewpoints of biocompatibility and affinity, CS and HA employed in the present invention are preferably alkali metal ion salts, particularly preferably sodium salts.

<S Orbitol>

"Sorbitol" herein is preferably D-sorbitol.

The concentration of sorbitol contained in the composition of the present invention is not particularly limited, but is preferably 0.1 mg/mL or higher, more preferably 0.5 mg/mL or higher, still more preferably 1 mg/mL or higher, and particularly preferably 2 mg/mL or higher. Since a higher content of sorbitol provides a higher suppressing effect on a viscosity drop of the aqueous composition containing CS and HA, the upper limit of the sorbitol concentration of the composition of the present invention is not particularly limited. However, examples of the upper limit of the sorbitol concentration of the composition of the present invention include 100 mg/mL or lower, 80 mg/mL or lower, 50 mg/mL or lower, 20 mg/mL or lower, and 10 mg/mL or lower. The concentration of sorbitol contained in the composition of the present invention is not particularly limited, but is, for example, 0.5 to 100 mg/mL, 1 to 80 mg/mL, 2 to 40 mg/mL, 2.5 to 20 mg/mL, or 5 to 10 mg/mL.

The sorbitol content is, with respect to 100 parts by mass of the total of CS and HA, preferably 0.5 to 120 parts by mass, more preferably 1 to 60 parts by mass, still more preferably 1.4 to 30 parts by mass, and particularly preferably 3 to 20 parts by mass.

<Pharmaceutically Acceptable Carrier>

Herein, examples of the "pharmaceutically acceptable carrier" include physiological saline, phosphate buffered saline, phosphate buffer, purified water, and water for injection, etc. Additives generally used in the art such as a pH-adjuster, a buffer, a tonicity agent, and an antiseptic may be suitably used. Examples of additives other than sorbitol include sodium chloride, potassium chloride, sodium dihydrogenphosphate, disodium hydrogenphosphate, sodium hydrogenphosphate, and monopotassium hydrogenphosphate. The composition of the present invention may contain no tris(hydroxymethyl)aminomethane and/or glycerin.

<Aqueous Composition>

The "aqueous composition" herein is not particularly limited so long as the composition contains water in an amount of 50% (w/v) or more. The composition of the present invention preferably has a water content of 80% (w/v) or higher, more preferably 90% (w/v) or higher.

<CS Concentration and HA Concentration>

According to U.S. Pat. No. 6,051,560, which discloses a viscoelastic composition containing CS and HA, interaction between CS and HA occur at any concentrations thereof. Thus, the CS concentration and HA concentration of the composition of the present invention are not particularly limited, and the CS concentration and HA concentration are individually exemplified as follows. Specifically, the CS concentration is preferably 10 to 100 mg/mL, more preferably 20 to 60 mg/mL, still more preferably 25 to 55 mg/mL, yet more preferably 30 to 50 mg/mL, further more preferably 35 to 45 mg/mL, and particularly preferably 40 mg/mL. The HA concentration is preferably 5 to 50 mg/mL, more preferably 10 to 40 mg/mL, still more preferably 15 to 35 mg/mL, yet more preferably 25 to 35 mg/mL, further more preferably 27 to 33 mg/mL, and particularly preferably 30 mg/mL. When CS and HA are at concentrations as described above, the aqueous composition can exhibit a certain level of viscosity. Such concentrations are preferred when the aqueous composition is used as ophthalmic compositions, inter alia, an ophthalmic surgical aid and/or an ophthalmic viscoelastic agent.

<Ratio of HA to CS>

The ratio of HA to CS is not particularly limited, but the ratio of HA with respect to 10 parts by mass of CS is preferably 1 to 20 parts by mass, more preferably 3 to 10 parts by mass, still more preferably 4 to 8 parts by mass, particularly preferably 7 to 8 parts by mass, and most preferably 7.5 parts by mass. A ratio of HA to CS falling within the above ranges is preferable for the aqueous composition to exhibit a certain level of viscosity. Such a ratio is preferred when the aqueous composition is used as ophthalmic compositions, inter alia, an ophthalmic surgical aid and/or an ophthalmic viscoelastic agent.

<pH>

The pH of the composition of the present invention is not particularly limited, but is preferably 6.0 to 8.0, more preferably 6.5 to 7.8, still more preferably 6.8 to 7.6, and particularly preferably 7.0 to 7.5.

<Viscosity>

The viscosity of the composition of the present invention may be determined by the method disclosed in the Examples. The "percent viscosity retention" (%) is calculated by the following formula (A). For example, when the viscosity at the start of storage is 50 Pa·s, and the viscosity at the time of evaluation is 30 Pas, the percent viscosity retention is 60%.

[MF1]

$$\text{Percent viscosity retention}=100\times(\text{viscosity at time of evaluation})/(\text{viscosity at start of storage}) \quad (A)$$

In addition, the "percent improvement in viscosity retention" (%) is calculated by the following formula (B). The "negative control sample" in this formula refers to the same sample as the evaluation sample except that the control sample does not contain an additive to be evaluated. For example, when the percent viscosity retention of the negative control sample is 25% at a given evaluation timing, and the percent viscosity retention of the evaluation sample is 50% at the same evaluation timing, the percent improvement in viscosity retention is 200%.

[MF2]

$$\text{Percent improvement in viscosity retention} = 100 \times \text{(percent viscosity retention of evaluation sample)/(percent viscosity retention of negative control sample)} \quad (B)$$

The viscosity of the composition of the present invention is not particularly limited, but is preferably 20,000 to 120,000 mPas, more preferably 30,000 to 110,000 mPas, still more preferably 35,000 to 80,000 mPas, and particularly preferably 35,000 to 60,000 mPas. The percent viscosity retention of the composition of the present invention after being stored for 6 months in the dark at 40° C. and an RH of 2.5% is not particularly limited, but is preferably 55% or higher, more preferably 60% or higher, still more preferably 65% or higher, and particularly preferably 70% or higher. The percent viscosity retention of the composition of the present invention after being stored for 24 months in the dark at 25° C. and an RH of 60% is not particularly limited, but is preferably 60% or higher, more preferably 70% or higher, still more preferably 80% or higher, and particularly preferably 85% or higher.

<Stabilization of Composition>

In the present invention, the term "stabilization of a composition" refers to stabilization of the viscosity of the composition. More specifically, the term means that the viscosity of the composition is maintained within a specific range, and preferably means that a drop in viscosity of the composition is suppressed. Stabilization of viscosity includes stabilization of the viscosity of the composition at room temperature and/or under exposure to light.

The degree of viscosity stabilization may be assessed using an index such as the aforementioned percent viscosity retention. In one embodiment where the percent viscosity retention falls within the aforementioned ranges, stabilization of the composition can be evaluated as being attained even at room temperature.

Herein, the terms "stability" of the composition and "stable (stably)" are also used with the same meaning as "stabilization".

In addition, the term "can be stored at room temperature" herein means that the viscosity of the composition is maintained within a specific range at room temperature.

From the viewpoint of the aforementioned percent viscosity retention, a specific example of the composition which "can be stored at room temperature" is a composition having a percent viscosity retention of preferably 55% or higher, more preferably 60% or higher, still more preferably 65% or higher, and particularly preferably 70% or higher, after being stored for 6 months in the dark at 40° C. and an RH of 25%. Another specific example of the composition is a composition having a percent viscosity retention of preferably 60% or higher, more preferably 70% or higher, still more preferably 80% or higher, and particularly preferably 85% or higher, after being stored for 24 months in the dark at 25° C. and an RH of 60%.

<Storage of Composition>

In the present invention, the term "storage of a composition" refers to keeping the composition in a container or the like.

Storage of the composition includes, for example, various steps: e.g., storage of the composition immediately after production thereof, during transportation thereof, and prior to use thereof by a user of the composition, as well as storage of the composition immediately before surgery or another treatment.

<Osmotic Pressure>

The ratio of osmotic pressure of the composition of the present invention to that of physiological saline is not particularly limited, but is preferably 0.8 to 1.4, and particularly preferably 0.9 to 1.3.

<Dosage Form>

The dosage form of the composition of the present invention is not particularly limited, and examples thereof include injections and eye drops. Of these, injections are preferred. The injections include, for example, those in the form of pre-filled syringes filled with the composition of the present invention.

<Form>

The form of the composition of the present invention is not particularly limited, but a solution or gel is preferred in that it can be used for injection, eye drop, application, or the like. Although the details will be described hereinbelow, the composition of the present invention is preferably colorless or clear.

<Room Temperature and Normal Temperature>

In the present invention, the term "room temperature" refers to a temperature of preferably about 0 to about 40° C., more preferably about 0 to about 35° C., and still more preferably about 1 to about 30° C.

In the present invention, the term "normal temperature" refers to a temperature of preferably about 10 to about 30° C., more preferably about 15 to about 25° C.

(2) Method for Producing the Composition of the Present Invention

The method for producing the aqueous composition of the present invention containing CS and HA is not particularly limited so long as the production method includes a step of including sorbitol in the composition. The method for producing a composition containing CS and HA is not particularly limited, but the composition can be produced, for example, in accordance with the method disclosed in U.S. Pat. No. 6,051,560. The method for producing the composition of the present invention includes, for example, a method of including CS, HA, sorbitol, and a pharmaceutically acceptable carrier. These ingredients may be mixed after being separately dissolved in a solvent, or mixed by sequentially adding each ingredient to a solvent. In this production method, the descriptions, examples, preferred ranges, etc. in the aforementioned "(1) Composition of the present invention" are directly applicable.

(3) Method of Use of the Composition of the Present Invention

<Use>

The use of the composition of the present invention is not particularly limited, but the composition is preferably used as an ophthalmic composition for ophthalmic purposes, particularly as an ophthalmic surgical aid, and more preferably as an ophthalmic viscoelastic agent or an OVD (ophthalmic viscosurgical device). In addition, since a drop in viscosity of the composition of the present invention is suppressed at room temperature and even at normal temperature by addition of sorbitol, the composition of the present invention can be practically used as a viscoelastic agent. Examples of the viscoelastic agent include an ophthalmic viscoelastic agent.

When the composition of the present invention is used as an ophthalmic surgical aid and/or an ophthalmic viscoelastic agent, the composition is preferably used as an aid for cataract surgery, and more preferably as an aid for cataract removal surgery and/or intraocular lens insertion. As necessary, the composition of the present invention may be used as a coating for intraocular lenses.

When the composition of the present invention is used for any of the aforementioned purposes, the composition may contain CS and/or HA as an active ingredient. When the composition of the present invention is used as an ophthalmic surgical aid and/or an ophthalmic viscoelastic agent, the composition of the present invention is preferably clear and colorless in order to ensure visibility of the interior of the eye, i.e. the surgical field.

<Administration Method>

The composition of the present invention may be used by administration to a patient, which includes animals including human. When the composition of the present invention is used for ophthalmic purposes, the administration method is not particularly limited so long as it is performed in a medically acceptable manner for administration to the eyes of an animal. The specific administration method is not particularly limited, but is preferably eye drop instillation or intraocular injection. Of these, intraocular injection is more preferred. Particularly preferred intraocular injection is anterior chamber injection.

<Dose>

The dose of the composition of the present invention may be appropriately selected in accordance with use of the composition. When the composition of the present invention is used as an ophthalmic surgical aid and/or an ophthalmic viscoelastic agent, the dose of the composition is not particularly limited, but is preferably 0.05 to 2 mL, more preferably 0.1 to 1 mL, and still more preferably 0.1 to 0.4 mL. In particular, at the time of cataract removal and/or at the time of intraocular lens insertion, each dose of 0.1 to 0.4 mL may be separately injected to the anterior chamber. In addition, 0.1 to 0.2 mL of the composition may be used for coating of an intraocular lens.

<Treatment Method>

Among the aforementioned uses, the aqueous composition of the present invention may be used in a method for treating an ocular disease, which method comprises a step of administering an effective amount of the aqueous composition to a patient in need of an ophthalmic surgical aid in an ophthalmic surgery.

The treatment method preferably includes, before the above step, a step of storing the aqueous composition of the present invention at room temperature.

This storing step may include a step of storing the composition immediately after production thereof, during transportation thereof, and prior to use thereof by a user of the composition, and a step of storing the composition immediately before surgery or another treatment.

Examples of the ocular disease include cataract.

In the above-mentioned treatment method, the descriptions, examples, preferred ranges, etc. in the aforementioned "(1) Composition of the present invention," the below-mentioned "(4) Stabilization method of the present invention," and the below-mentioned "(5) Storage method of the present invention" are directly applicable.

<Other Modes of Use>

Among the aforementioned uses, the aqueous composition of the present invention may be applied to use of the aqueous composition for producing an ophthalmic surgical aid employed in an ophthalmic surgery.

In this case, the aqueous composition is preferably an aqueous composition for use in an ophthalmic surgery after storage thereof at room temperature.

Also, the aqueous composition of the present invention may be applied for use as an ophthalmic surgical aid employed in an ophthalmic surgery for the treatment of an ocular disease.

In this case, the aqueous composition is preferably an aqueous composition for use in an ophthalmic surgery after storage thereof at room temperature.

The storing step may include a step of storing the composition immediately after production thereof, during transportation thereof, and prior to use thereof by a user of the composition, and a step of storing the composition immediately before surgery or another treatment.

Examples of the ocular disease include cataract.

In the above-mentioned use, the descriptions, examples, preferred ranges, etc. described in the aforementioned "(1) Composition of the present invention," the below-mentioned "(4) Stabilization method of the present invention," and the below-mentioned "(5) Storage method of the present invention" are directly applicable.

(4) Stabilization Method of the Present Invention

The method for stabilizing an aqueous composition of the present invention is a method for stabilizing an aqueous composition which comprises CS, HA, and a pharmaceutically acceptable carrier and which can be stored at room temperature.

Furthermore, the method for stabilizing an aqueous composition of the present invention is a method for stabilizing an aqueous composition comprising CS and HA by including sorbitol in the composition.

In this stabilization method, the descriptions, examples, preferred ranges, etc. described in the aforementioned "(1) Composition of the present invention" are directly applicable.

The aqueous composition stabilization method of the present invention allows stable storage of an aqueous composition.

In the stabilization method of the present invention, it is preferred to store an aqueous composition at room temperature. The method allows stable storage of the aqueous composition and can suppress a drop in viscosity of the composition even at room temperature for a long period of time.

In one embodiment, the aforementioned stabilization method allows stable storage of the composition either with or without protection from light. For example, the method allows stable storage of the aqueous composition and can suppress a drop in viscosity of the composition even without protection from light.

(5) Storage Method of the Present Invention

The method for storing an aqueous composition of the present invention is a method for storing an aqueous composition which comprises CS, HA, and a pharmaceutically acceptable carrier and which can be stored at room temperature.

Furthermore, the method for storing an aqueous composition of the present invention is a method for storing an aqueous composition comprising CS and HA by incorporating sorbitol into the composition.

The aqueous composition to be stored is the aqueous composition described in the aforementioned "(1) Composition of the present invention," and the descriptions, examples, preferred ranges, etc. described therein are directly applicable.

In the aqueous composition storage method of the present invention, the composition can be stably stored at any stage before use thereof, at room temperature, normal temperature, or a temperature higher than room temperature. For example, the composition can be stably stored even at a temperature higher than 8° C. The meaning of the term "stable (stably)" is as defined in the aforementioned "Stabilization of composition." In the aqueous composition storage method of the present invention, the aqueous composition is preferably stored at room temperature.

In one embodiment, the aforementioned storage method allows stable storage of the composition either with or without protection from light. For example, the method allows stable storage of the aqueous composition and can suppress a drop in viscosity of the composition even without protection from light.

The storage period of the aqueous composition is not particularly limited, and may be freely determined in accordance with the mode of use of the composition, time of transportation, etc. For example, the storage period may be a short period of up to 24 hours immediately after production of the aqueous composition, a medium long period of 1 day to 6 months, or a long period of 6 months or longer.

The aqueous composition storage method of the present invention may include a step of storing the composition immediately after production thereof, during transportation thereof, prior to use thereof by a user of the composition, and storing the composition immediately before surgery or another treatment. In the present invention, the aqueous composition can be stored immediately after production thereof, during transportation thereof, and prior to being used by a user of the composition. In other words, the composition of the present invention is not required to be stored at low temperature, which makes it unnecessary to warm the composition up to room temperature immediately before use.

The container for storing the aqueous composition is not particularly limited, and a generally known container may be employed. A sealable container is preferred.

The present invention will next be described in more detail by way of the Examples and the Test Examples, which should not be construed as limiting the invention thereto.

EXAMPLES

Example 1: Storage Stability (at 60° C.) Test (1) Preparation of Phosphate Buffer Sodium dihydrogenphosphate dihydrate (0.509 g), disodium hydrogenphosphate dodecahydrate (5.04 g), and sodium chloride (4.30 g) were dissolved in water for injection, and the total volume was adjusted to 1,000 g to prepare a phosphate buffer (hereinafter also referred to as "PBS"). Each weight value refers to a relative weight.

(2) Preparation of Aqueous Composition Containing CS and HA

Sodium hyaluronate (weight average molecular weight: about 900,000, product of Seikagaku Corporation) was treated with heat to reduce its molecular weight, yielding sodium hyaluronate with a weight average molecular weight of about 700,000. This sodium hyaluronate, chondroitin sulfate sodium (weight average molecular weight; about 20,000, product of Seikagaku Corporation), and an additive were mixed together at proportions shown in Table 1 to prepare aqueous compositions. The employed additives were D-sorbitol (EP, product of Wako Pure Chemical), glycine (GR, product of Wako Pure Chemical), L-glutamic acid (GR, product of Wako Pure Chemical), sodium L-glutamate (Japanese Pharmaceutical Codex, product of Wako Pure Chemical), and L-methionine (GR, product of Wako Pure Chemical). PBS was used as a solvent. The numerical values in Table 1 represent the amount of each ingredient contained in 1 mL of each composition. The symbol "−" indicates that the composition does not contain the relevant ingredient.

TABLE 1

| Ingredients | Formulation 1 | Formulation 2 | Formulation 3 | Formulation 4 | Formulation 5 | Formulation 6 |
|---|---|---|---|---|---|---|
| CS (mg) | 40 | 40 | 40 | 40 | 40 | 40 |
| HA (mg) | 30 | 30 | 30 | 30 | 30 | 30 |
| D-Sorbitol (mg) | — | 5 | — | — | — | — |
| Glycine (mg) | — | — | 5 | — | — | — |
| L-Glutamic acid (mg) | — | — | — | 5 | — | — |
| Na L-glutamate (mg) | — | — | — | — | 5 | — |
| L-Methionine (mg) | — | — | — | — | — | 5 |

(3) Test Method

Each of the compositions of Formulations 1 to 6 was stored in the dark at 60° C. for 14 days. The viscosity of each composition was measured at the start of storage and on day 3, day 7, day 10, and day 14 of the storage. The viscosity of each formulation at each timing was compared with the viscosity of Formulation 1 (additive-free) at the start of storage, whereby the effect of the additive on the viscosity of the composition was assessed. On day 14, the status of browning was checked.

Viscosity Measurement

A rotary viscometer (model: TVE-22H, product of Toki Sangyo Co., Ltd.) was employed. The viscosity of the composition at 25° C. and a shear rate of 2 s$^{-1}$ was measured at each time point.

Assessment of Browning

The browning status of each composition was visually checked 14 days after start of storage and evaluated by scoring in accordance with the following ratings.

<Ratings>

"−" Browning lighter than that of Formulation 1 (negative control)

"±" Browning equivalent to that of Formulation 1 (negative control)

"+" Browning heavier than that of Formulation 1 (negative control)

(4) Results

Table 2 shows the results.

TABLE 2

|  | Formulation 1 | Formulation 2 | Formulation 3 | Formulation 4 | Formulation 5 | Formulation 6 |
|---|---|---|---|---|---|---|
| Additive | None | Sorbitol | Glycine | Glutamic acid | Na glutamate | Methionine |
| Viscosity (Pa · s), day 0 | 50.54 | – | – | – | – | – |
| Viscosity (Pa · s), day 3 | 41.64 | 44.83 | 8.49 | 10.43 | 26.77 | 40.44 |
| Viscosity (Pa · s), day 7 | 27.56 | 36.10 | 1.07 | 0.99 | 8.64 | 29.61 |
| Viscosity (Pa · s), day 10 | 20.61 | 28.91 | 0.05 | 0.08 | 4.37 | 23.85 |
| Viscosity (Pa · s), day 14 | 16.76 | 25.53 | 0 | 0 | 2.51 | 18.73 |
| Browning, day 14 | ± | ± | + | + | ± | ± |

"–": No data

All the formulations containing CA and HA and containing glycine, L-glutamic acid, or Na L-glutamate, which was reported in Japanese Patent Application Laid-Open (kokai) No. 1999-302197 to stabilize HA, exhibited a viscosity definitely lower than that of Formulation 1 (negative control) at all timings of storage. As a result, these additives were found to accelerate a drop in viscosity of the aqueous composition containing CS and HA. Formulation 6 containing L-methionine, which is used as a stabilizer of a commercial hyaluronic acid preparation (Suvenyl®), exhibited a viscosity almost equivalent to that of Formulation 1 at all timings, indicating that the effect of Formulation 6 on suppressing a viscosity drop was not significant. Browning of Formulation 6 was more significant as compared with Formulation 1, indicating that L-methionine promoted browning. In contrast, Formulation 2, containing D-sorbitol, exhibited a viscosity higher than that of Formulation 1 at all timings. Browning of Formulation 2 was not accelerated by D-sorbitol contained therein. Accordingly, sorbitol has been found to suppress a drop in viscosity of an aqueous composition containing CS and HA and to serve as a remarkably useful stabilizer for the composition.

These results also suggest that a composition containing both CS and HA shows different behavior from that of a composition containing only HA.

Example 2: Storage Stability (at 60° C.) Test

Using glucose (GR, product of Wako Pure Chemical), maltose hydrate (GR, product of Wako Pure Chemical), xylitol (GR, product of Wako Pure Chemical), or condensed mixed tocopherol (EP, product of Wako Pure Chemical) as an additive, aqueous compositions were prepared and tested to evaluate the effect of each additive on the viscosity of the composition and check the browning status under the same conditions as Example 1, including the procedure, amounts (CS: 40 mg, HA: 30 mg, and additive: 5 mg) and experimental conditions. Table 3 shows the results.

TABLE 3

|  | Formulation 7 | Formulation 8 | Formulation 9 | Formulation 10 |
|---|---|---|---|---|
| Additive | Glucose | Maltose hydrate | Xylitol | Tocopherol |
| Viscosity (Pa · s), day 0 | – | – | – | – |
| Viscosity (Pa · s), day 3 | 38.92 | 43.70 | 44.66 | 38.22 |
| Viscosity (Pa · s), day 7 | 22.73 | 29.77 | 32.49 | 25.68 |
| Viscosity (Pa · s), day 10 | 15.59 | 22.88 | 26.69 | 19.99 |
| Viscosity (Pa · s), day 14 | 9.37 | 17.31 | 19.33 | 15.85 |
| Browning, day 14 | ± | ± | ± | ± |

The viscosity values of Formulations 8, 9, and 10, containing CS and HA, and containing maltose hydrate, xylitol, or tocopherol as an additive, were almost equivalent to the viscosity of Formulation 1, indicating that these additives had a small effect on suppressing a viscosity drop. Formulation 7, containing glucose as an additive, exhibited a considerable viscosity drop. Xylitol in Formulation 9 exhibited a drastic drop in viscosity on day 14. In contrast, Formulation 2, containing D-sorbitol, exhibited a viscosity higher than that of Formulation 1 at all timings as described above, and its browning was not accelerated by D-sorbitol contained therein. Accordingly, sorbitol has been found to suppress a drop in viscosity of an aqueous composition containing CS and HA and to serve as a remarkably useful stabilizer for the composition.

Example 3: Study on Sorbitol Concentration (1) Test Method

In a manner similar to that of Example 1, aqueous compositions of the formulations shown in Table 4 were prepared. Each of the numerical values in Table 4 represents an amount of each ingredient contained in 1 mL of the composition. The symbol "–" indicates that the composition does not contain the relevant ingredient.

TABLE 4

| Ingredients | Formulation 11 | Formulation 12 | Formulation 13 | Formulation 14 |
|---|---|---|---|---|
| CS (mg) | 40 | 40 | 40 | 40 |
| HA (mg) | 30 | 30 | 30 | 30 |
| D-Sorbitol (mg) | — | 1 | 5 | 10 |

The viscosity of each of the compositions of Formulations 11 to 14 before and after a heat treatment (121° C., 5 minutes) was measured in accordance with Example 1. In each case, percent viscosity retention and percent improvement in viscosity retention were calculated from the measurement results.

(2) Results

Table 5 shows the results.

TABLE 5

|  | Formulation 11 | Formulation 12 | Formulation 13 | Formulation 14 |
|---|---|---|---|---|
| Additive | None | Sorbitol 0.1% (w/v) | Sorbitol 0.5% (w/v) | Sorbitol 1% (w/v) |
| Viscosity (Pa · s), before heat treatment | 75.93 | 70.91 | 71.76 | 72.83 |
| Viscosity (Pa · s), after heat treatment | 37.24 | 41.05 | 47.15 | 49.50 |
| Viscosity retention (%) | 49.0 | 57.9 | 65.7 | 68.0 |
| Improvement in viscosity retention (%) | 100 | 118 | 134 | 139 |

As shown in Table 5, the percent viscosity retention of Formulation 11 (negative control) decreased after the heat treatment (121° C., 5 minutes). In contrast, Formulations 12 to 14, each containing D-sorbitol, exhibited a percent viscosity retention higher than that of the negative control. As a result, the above procedure has been found to be effective for evaluating the action of D-sorbitol on suppressing a viscosity drop. In addition, the viscosity drop-suppressing effect of sorbitol on the composition of the present invention has been found to be exhibited within a sorbitol concentration range of 0.1% to 1% (w/v).

Next, the viscosity drop suppressing action at higher sorbitol concentration was investigated. Firstly, compositions containing D-sorbitol at a concentration of 0.25%, 0.5%, 1%, 2%, 4%, or 8% (w/v) were prepared in accordance with Example 1. Each of the thus-prepared compositions was stored at 60° C. for 14 days in the dark. The viscosity of the composition was measured at the start of storage and on day 14 of storage, and percent improvement in viscosity retention was calculated. As a result, percent improvement in viscosity retention at D-sorbitol concentrations of 0.25%, 0.5%, 1%, 2%, 4%, and 8% were 175%, 181%, 191%, 178%, 263%, and 300%, respectively. Thus, as the D-sorbitol content increased, a drop in viscosity of the compositions was more effectively suppressed.

The above experiments have revealed that the viscosity drop-suppressing effect of D-sorbitol can be attained at least within a wide sorbitol concentration range of 0.1% (1 mg/mL) to 8% (80 mg/mL).

Example 4: Photostability Test (1) Test Method

In accordance with Example 1, aqueous compositions of the formulations shown in Table 6 were prepared. Each of the numerical values in Table 6 represents an amount of each ingredient contained in 1 mL of the composition. The symbol "–" indicates that the composition does not contain the relevant ingredient.

TABLE 6

| Ingredients | Formulation 15 | Formulation 16 | Formulation 17 |
|---|---|---|---|
| CS (mg) | 40 | 40 | 40 |
| HA (mg) | 30 | 30 | 30 |
| D-Sorbitol (mg) | — | 5 | 10 |

Each of the compositions of Formulations 15 to 17 was loaded into a plastic syringe (product of Schott) and exposed to light at 1,200,000 lx·hr. More specifically, the syringe was set in a photostability tester (model: LT-120 D3J, product of Nagano Science) and irradiated with light (2,000 lx/hr) for 25 days at 25° C. The viscosity of the composition was measured before and after light exposure in accordance with Example 1, and percent viscosity retention was calculated. A syringe protected from light with aluminum foil was employed as a control.

(2) Results

Table 7 shows the results.

TABLE 7

|  | Formulation 15 | | Formulation 16 | | Formulation 17 | |
|---|---|---|---|---|---|---|
| Additive |  |  |  |  |  |  |
|  | None | | D-Sorbitol 0.5% (w/v) | | D-Sorbitol 1% (w/v) | |
| Light protection |  |  |  |  |  |  |
|  | No | Yes | No | Yes | No | Yes |
| Viscosity (Pa · s), before light exposure | 57.78 | 57.78 | 57.61 | 57.61 | 56.87 | 56.87 |
| Viscosity (Pa · s), after light exposure | 49.62 | 53.26 | 52.87 | 53.93 | 54.47 | 55.10 |
| Viscosity retention (%) | 85.9 | 92.2 | 91.8 | 93.6 | 95.8 | 96.9 |

As shown in Table 7, a drop in viscosity due to light exposure was suppressed in Formulations 16 and 17, containing D-sorbitol, as compared with Formulation 15 (control). Thus, the test has revealed that inclusion of D-sorbitol can enhance stability of the composition against light.

Example 5: Long-Term Stability Test (1) Test Method

An aqueous composition containing CS, HA, and D-sorbitol was prepared in accordance with Example 1 and loaded into a syringe (made of polyolefin). This syringe was stored in the dark at 25° C. and an RH of 60%. At the start of storage and on month 3, month 6, month 9, month 12, month 18, and month 24 of the storage, the viscosity of the composition was measured in accordance with Example 1, and percent viscosity retention was calculated.

(2) Results

The percent viscosity retention values on month 3, month 6, month 9, month 12, month 18, and month 24 of the storage were 95.5%, 96.7%, 94.6%, 93.9%, 93.9%, and 90.0%, respectively. That is, high percent viscosity retention was observed. Thus, it has been shown that the composition of the present invention can be stably stored at room temperature for at least 24 months.

Example 6: Storage (at 40° C.) Stability Test (1) Test Method

An aqueous composition containing CS, HA, and D-sorbitol was prepared in accordance with Example 1 and loaded into a syringe (made of polyolefin). This syringe was stored in the dark at 40° C. and an RH of ≤2.5%. At the start of storage and 6 months after the storage, the viscosity of the composition was measured in accordance with Example 1, and percent viscosity retention was calculated.

(2) Results

At month 6 after the start of storage, the percent viscosity retention of the composition was 76.2%. That is, high percent viscosity retention was observed. Thus, it has been shown that the composition of the present invention exhibits high stability even at 40° C.

Example 7: Photostability Test (1) Test Method

An aqueous composition containing CS, HA, and D-sorbitol was prepared in accordance with Example 1 and loaded into a syringe (made of polyolefin). This syringe was set in a photostability tester (model: LT-120 D3J, product of Nagano Science) and irradiated with light (2,000 lx/hr) for 25 days at 25° C. (light exposure dose: 1,200,000 lx·hr, total near-UV radiation energy: 2.00 W·h/m$^2$). Before and after light exposure, the viscosity of the composition was measured in accordance with Example 1, and percent viscosity retention was calculated. A syringe protected from light with aluminum foil was employed as a control.

(2) Results

The percent viscosity retention values of the light exposure group and the light-protected group (control) were 95.4% and 97.6%, respectively. That is, high percent viscosity retention was observed. Thus, it has been shown that the composition of the present invention does not require light protection when being stored.

INDUSTRIAL APPLICABILITY

The composition of the present invention is industrially applicable because it is a stabilized aqueous composition containing CS and HA and therefore can be used as an ophthalmic composition, particularly, as an ophthalmic surgical aid.

The invention claimed is:

1. A method for stabilizing a viscosity of an aqueous composition during storage, wherein the method comprises adding sorbitol in an aqueous composition which comprises 30 to 50 mg/mL of chondroitin sulfate or a salt thereof, 25 to 35 mg/mL of hyaluronic acid or a salt thereof, and a pharmaceutically acceptable carrier, thereby stabilizing the aqueous composition at room temperature, wherein after storage for 24 months in the dark at 25° C. and an RH (relative humidity) of 60% the aqueous composition has a viscosity of 20,000 to 120,000 mPa·s at 25° C. and at shear rate of 2 s$^{-1}$ and wherein the aqueous composition is used for an ophthalmic surgical aid employed in an ophthalmic surgery for treating an ocular disease.

2. A method of manufacturing an aqueous composition, comprising mixing 30 to 50 mg/mL of chondroitin sulfate or a salt thereof, 25 to 35 mg/mL of hyaluronic acid or a salt thereof, sorbitol, and a pharmaceutically acceptable carrier, wherein after storage for 24 months in the dark at 25° C. and an RH (relative humidity) of 60% the aqueous composition has a viscosity of 20,000 to 120,000 mPa·s at 25° C. and at shear rate of 2 s$^{-1}$ and wherein the aqueous composition is used for an ophthalmic surgical aid employed in an ophthalmic surgery for treating an ocular disease.

3. The method of claim 1, wherein the sorbitol is D-sorbitol.

4. The method of claim 1, wherein the sorbitol concentration in the aqueous composition is 2 to 80 mg/mL.

5. The method of claim 1, wherein the concentration of the chondroitin sulfate or a salt thereof in the aqueous composition is 40 mg/mL, and the concentration of the hyaluronic acid or a salt thereof in the aqueous composition is 30 mg/mL.

6. The method of claim 2, wherein the concentration of the chondroitin sulfate or a salt thereof in the aqueous composition is 40 mg/mL, and the concentration of the hyaluronic acid or a salt thereof in the aqueous composition is 30 mg/mL.

7. The method of claim 2, wherein the sorbitol concentration in the aqueous composition is 20 mg/mL or lower.

8. The method of claim 1, wherein the sorbitol concentration in the aqueous composition is 10 mg/mL or lower.

9. The method of claim 1, wherein the sorbitol concentration in the aqueous composition is 2.5 to 20 mg/mL.

10. The method of claim 1, wherein the sorbitol concentration in the aqueous composition is 5 to 10 mg/mL.

11. The method of claim 1, wherein the sorbitol concentration in the aqueous composition is 5 mg/mL.

12. The method of claim 1, wherein the aqueous composition contains no tris(hydroxymethyl)aminomethane.

13. The method of claim 2, wherein the aqueous composition contains no tris(hydroxymethyl)aminomethane.

* * * * *